(12) United States Patent
Megerle et al.

(10) Patent No.: US 6,711,939 B2
(45) Date of Patent: Mar. 30, 2004

(54) METHOD AND SYSTEM FOR EXPELLING TEST-SAMPLE VOLUMES FROM LUGGAGE/PACKAGES

(75) Inventors: Clifford A. Megerle, Thousand Oaks, CA (US); Philip T. James, Bristow, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/183,414

(22) Filed: Jun. 28, 2002

(65) Prior Publication Data

US 2003/0106362 A1 Jun. 12, 2003

Related U.S. Application Data

(60) Provisional application No. 60/336,716, filed on Dec. 7, 2001.

(51) Int. Cl.$^7$ .................................................. G01M 3/04
(52) U.S. Cl. ...................................................... 73/45.4
(58) Field of Search ...................... 53/53, 437; 73/45.4, 73/49.3, 863.22

(56) References Cited

U.S. PATENT DOCUMENTS

| | | | |
|---|---|---|---|
| 4,024,956 A | * | 5/1977 | Cassidy ...................... 209/3.1 |
| 4,148,213 A | * | 4/1979 | Prakken ....................... 73/45.4 |
| 4,510,730 A | * | 4/1985 | Edmondson .................... 53/53 |
| 4,864,848 A | * | 9/1989 | Irvine ......................... 73/45.4 |
| 5,284,003 A | * | 2/1994 | Goodman et al. ............ 53/437 |
| 5,786,530 A | * | 7/1998 | Fenlon ........................ 73/49.3 |
| 6,105,419 A | * | 8/2000 | Michels et al. .............. 73/49.3 |
| 6,427,524 B1 | * | 8/2002 | Raspante et al. ............ 73/45.4 |
| 2002/0124664 A1 | * | 9/2002 | Call et al. ................ 73/863.22 |

* cited by examiner

Primary Examiner—Hezron Williams
(74) Attorney, Agent, or Firm—Wallace G. Walter

(57) ABSTRACT

A method and system for expelling test sample-volumes from luggage/packages includes, in one form, a set of superposed or otherwise cooperating belt conveyor (16, 24) and a cooperating biohazard detection system (14). Luggage articles (L) or packages to be inspected are moved by the belt conveyor (18) and subject to a momentary compressive force to reduce the internal volume of the luggage article or package sufficient to expel some of the interior air within the luggage article or package. The biohazard detection system (14) samples some of the air expelled from the interior of the luggage article (L) and subjects that air sample to various test of undesired or prohibited materials.

11 Claims, 9 Drawing Sheets

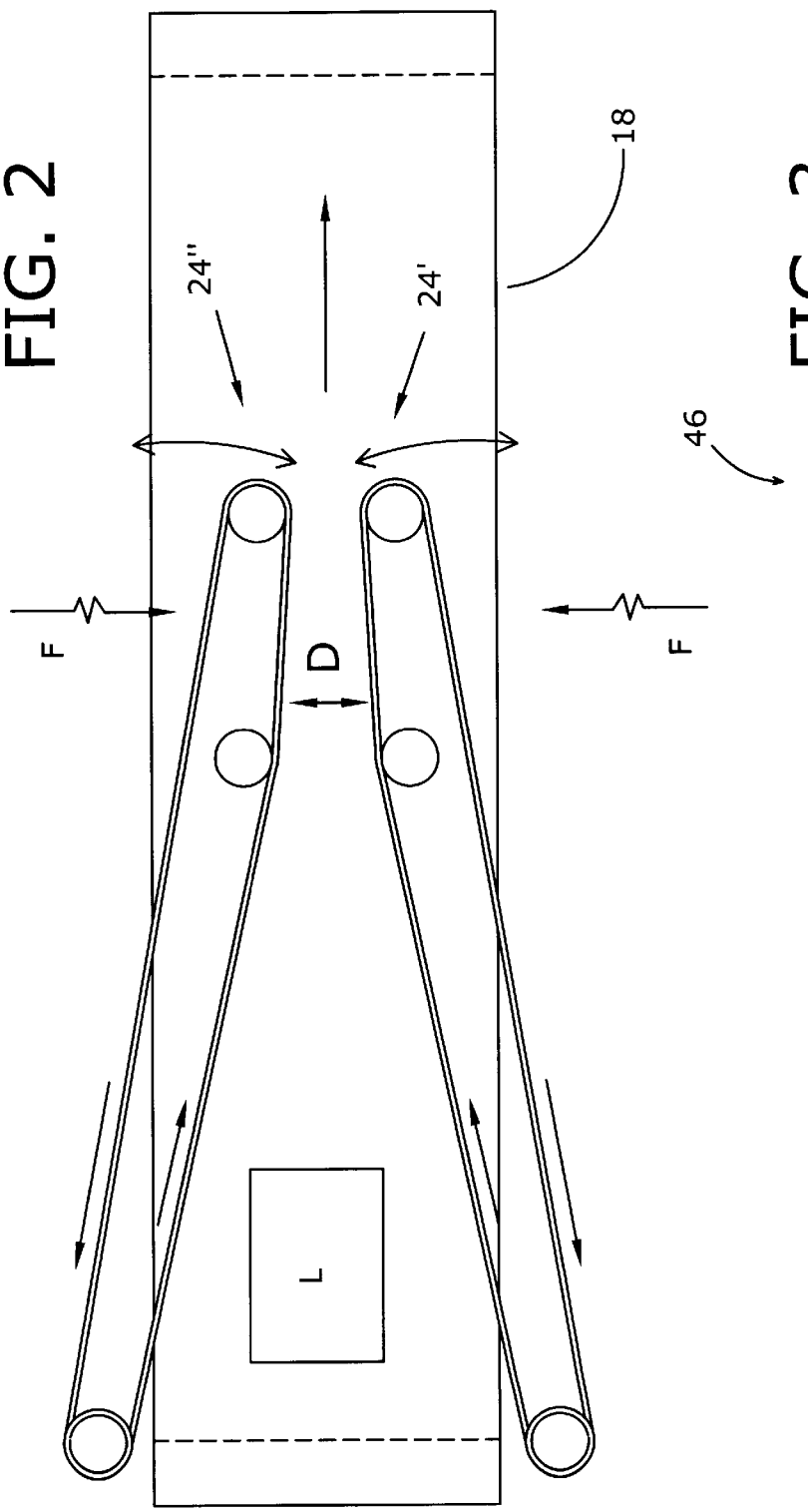

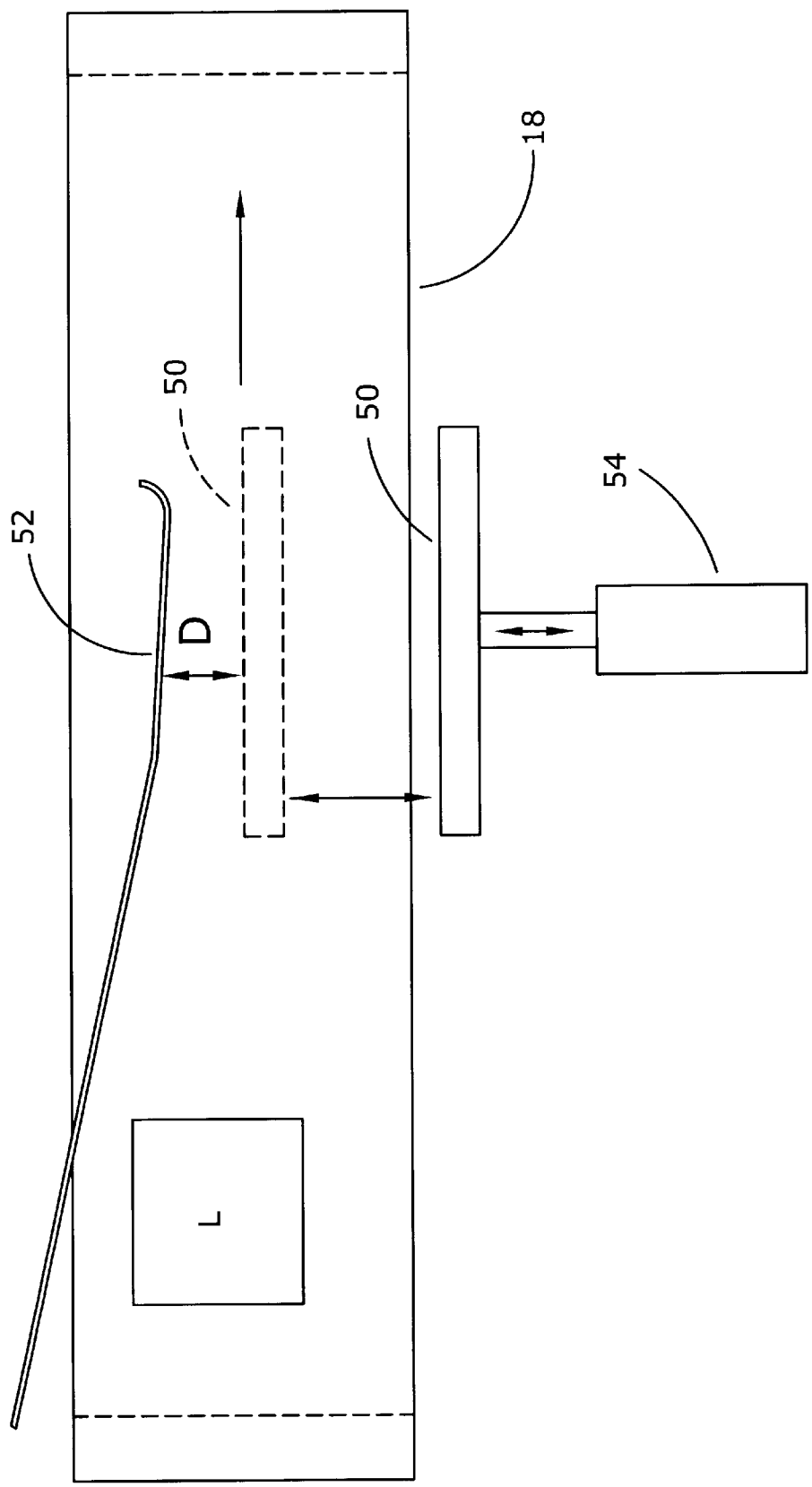

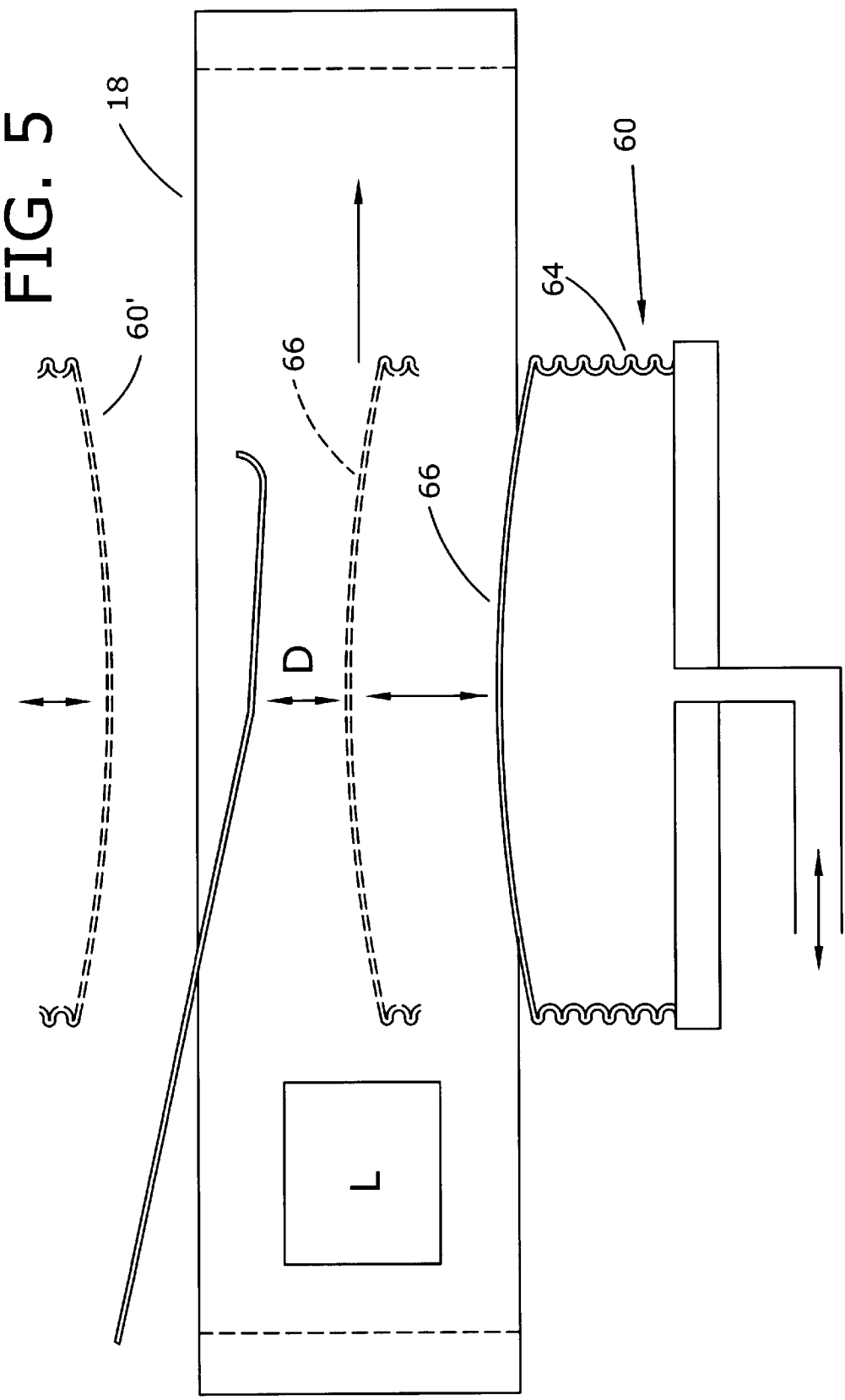

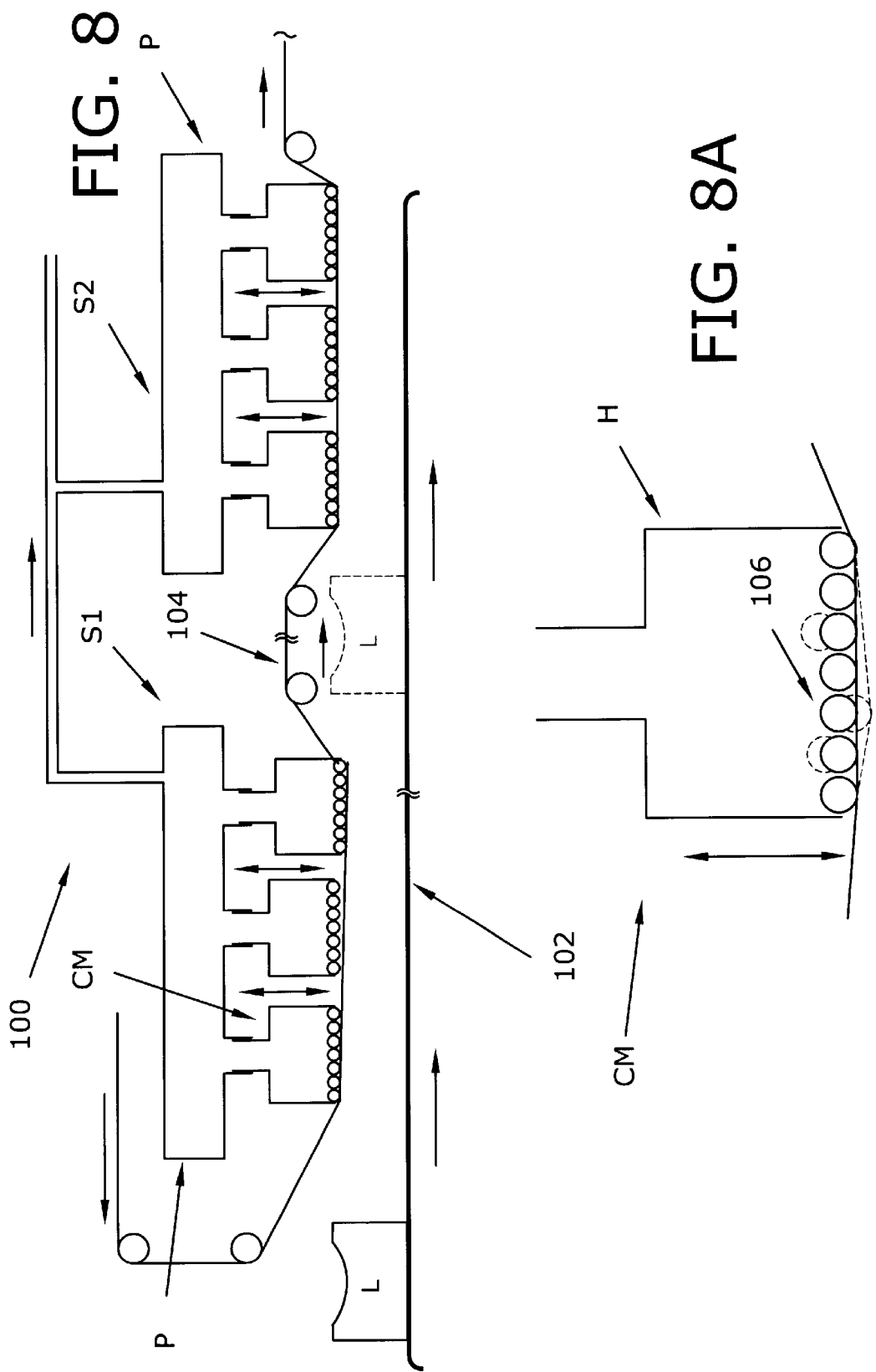

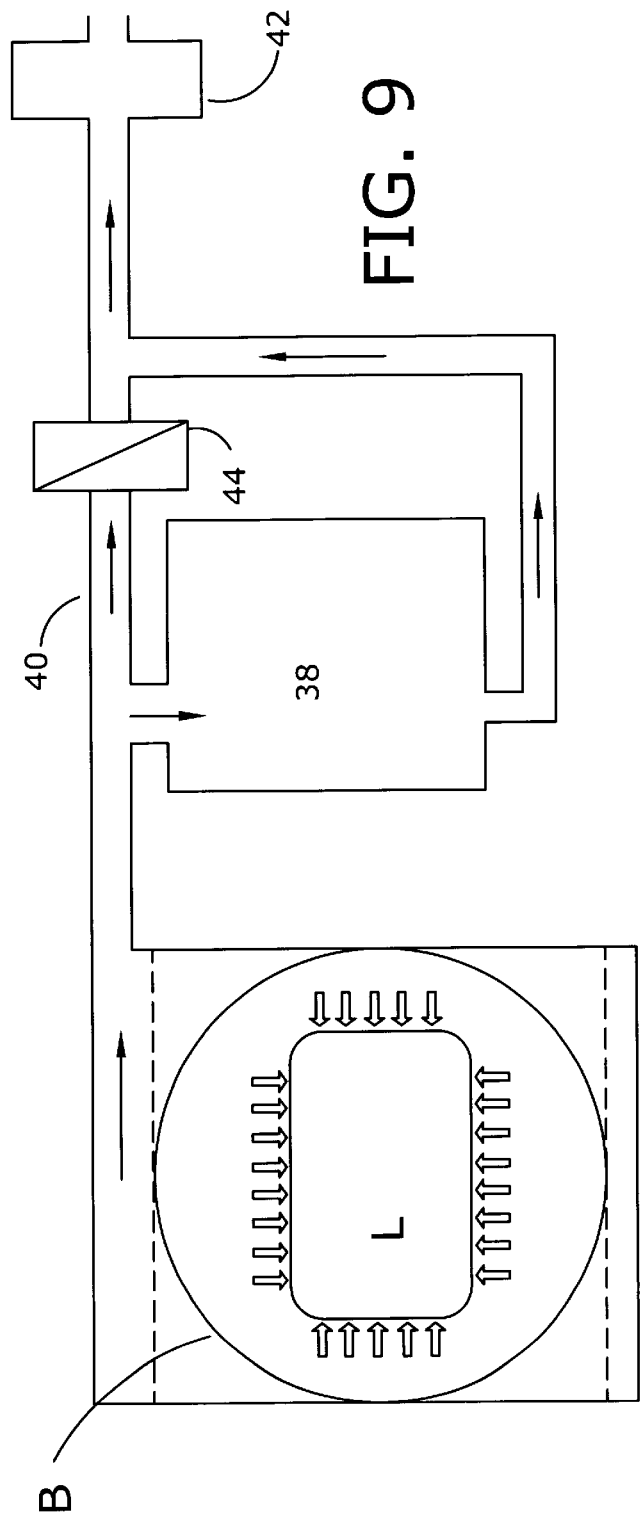

METHOD AND SYSTEM FOR EXPELLING TEST-SAMPLE VOLUMES FROM LUGGAGE/PACKAGES

BACKGROUND OF THE INVENTION

This application claims the benefit of U.S. Provisional Patent Application No. 60/336,716 filed Dec. 7, 2001 by the inventors herein.

The present invention relates to a method and system for expelling test sample-volumes from luggage articles and/or packages to test for the presence of explosives and/or biohazardous materials within each luggage article or package, and, more particularly, to a method and system for expelling or expressing a portion of the interior air volume of luggage articles or packages in a moving stream of such luggage articles or packages in the context, for example, of luggage conveyor/handling systems typically used at airports and other transportation hubs to test for explosives and/or biohazardous materials, particulates, and vapors.

The airport, rail, bus, and package handling transport systems typically handle large volumes of luggage and/or packages as part of their operations. For example, the airline system subjects 'carry-on' luggage, bags, packages, and the like to an X-ray inspection and, on occasion, to a hand search. Luggage, bags, packages, and the like that are 'checked' are identified with a particular ticketed passenger and then moved through a luggage routing system in which the individual luggage articles are directed to a particular aircraft for loading.

In general, it is considered beneficial to inspect each luggage article and/or package for dangerous or otherwise proscribed materials prior to being loaded into the luggage compartment of the aircraft. In practice, however, it is difficult to inspect each article of luggage or package, particularly those packages that may contain biohazards that are not directly visible to the eye.

Various types of sensors have been developed to sense the presence of explosives and/or biohazardous material particles or vapors suspended or entrained in air. While these types of sensors are effective for their intended design purpose, they are of limited value in detecting the presence of a hazardous in the interior volume of closed luggage articles and other packages.

SUMMARY OF THE INVENTION

In view of the above, it is an object of the present invention, among others, to provide a method and system for expelling test sample-volumes from luggage articles or packages for the detection of hazardous materials within the luggage articles or packages.

It is another object of the present invention to provide a method and system for expelling test sample-volumes from luggage articles or packages for the detection of hazardous materials within the luggage/packages that can effectively test a continuously moving stream or flow of moving luggage articles or packages.

In view of these objects, and others, the present invention provides a method and system for expelling test sample-volumes from luggage articles and packages in a moving stream of such articles and packages. In accordance with the present method, one or more luggage articles or packages in a stream of such articles or packages is subjected to one or more momentary compressions to reduce the interior air volume of the article or package to express or expel a portion of the interior air volume from the luggage article or package. A sensor system located in the vicinity of momentarily compressed article or package when it is subjected to its compressive force senses for the presence undesired materials, particularly biohazard materials.

In one general form of the invention, moving belt conveyors are arranged to resiliently press against each luggage article or package moved along a conveyor system to effect the desired momentary compression. In another general form of the invention, a pressing surface is momentarily advanced into engagement with the luggage article or package to effect the desired momentary compression. The pressing surface can be a mechanically driven 'presser' plate or, for example, a surface portion of a pneumatically actuated bellows. In other forms of the invention, the luggage article is subject to successive compression between moving belts or by the use of inflatable bladders that surround and forcibly engage various surfaces of the luggage article or package.

The sensor system can take the form, for example, of one or more sensors designed to detect one or more of a plurality of dangerous or proscribed materials, including explosives, explosives-related compounds, oxidizers, chemical warfare agents, illicit drugs, hazardous industrial chemicals, radioactive particles, and the like. Additionally, the sensor system can be equipped to detect biological pathogens or other undesired or prohibited materials, including but not limited to air-entrainable particles, including bacteria, bacterial spores, viruses, rickettsia, and toxins.

An air handling system can be co-located in the general vicinity of the system that effects the momentary compression of each luggage article or package to drawn in each test-volume sample expressed from the articles or packages for processing by the sensor system.

The present invention is best suited for use with luggage articles that are constructed from yieldable resilient materials including soft-sided luggage and fabric bags or carriers.

The present invention advantageously provides a method and system for expelling test sample-volumes from luggage article or packages in those contexts, such as an airline terminal, where a large number of articles in moving streams must be inspected on a continuous or near continuous basis.

Other objects and further scope of applicability of the present invention will become apparent from the detailed description to follow, taken in conjunction with the accompanying drawings, in which like parts are designated by like reference characters.

BRIEF DESCRIPTION OF THE DRAWING

FIG. 2 is a simplified top view of another embodiment of a system for expelling test sample-volumes from luggage/packages in accordance with the present invention;

FIG. 3 represents a structural variant of the embodiment of FIG. 2;

FIG. 4 is a simplified top view of another embodiment of a system for expelling test sample-volumes from luggage/packages using a mechanically reciprocating 'pusher' plate;

FIG. 5 is a simplified top view of another embodiment of a system for expelling test sample-volumes from luggage/packages using a fluidically expansible bellows structure;

FIG. 8 is a side elevation view, in pictorial form, of a multiple-station embodiment for subjecting luggage articles and packages of irregular form to successive compressions between superposed moving belts;

FIG. 8A is a detail view of a portion of FIG. 8;

FIG. 9 is one example of an expansible compression 'cuff' or bladder by which multiple sides of a luggage article or package are subjected to a compression force;

FIG. 9A is an idealized representation of an exemplary surface texture/structure for the 'cuff' of FIG. 9;

DESCRIPTION OF THE PREFERRED EMBODIMENT

Figure 1:
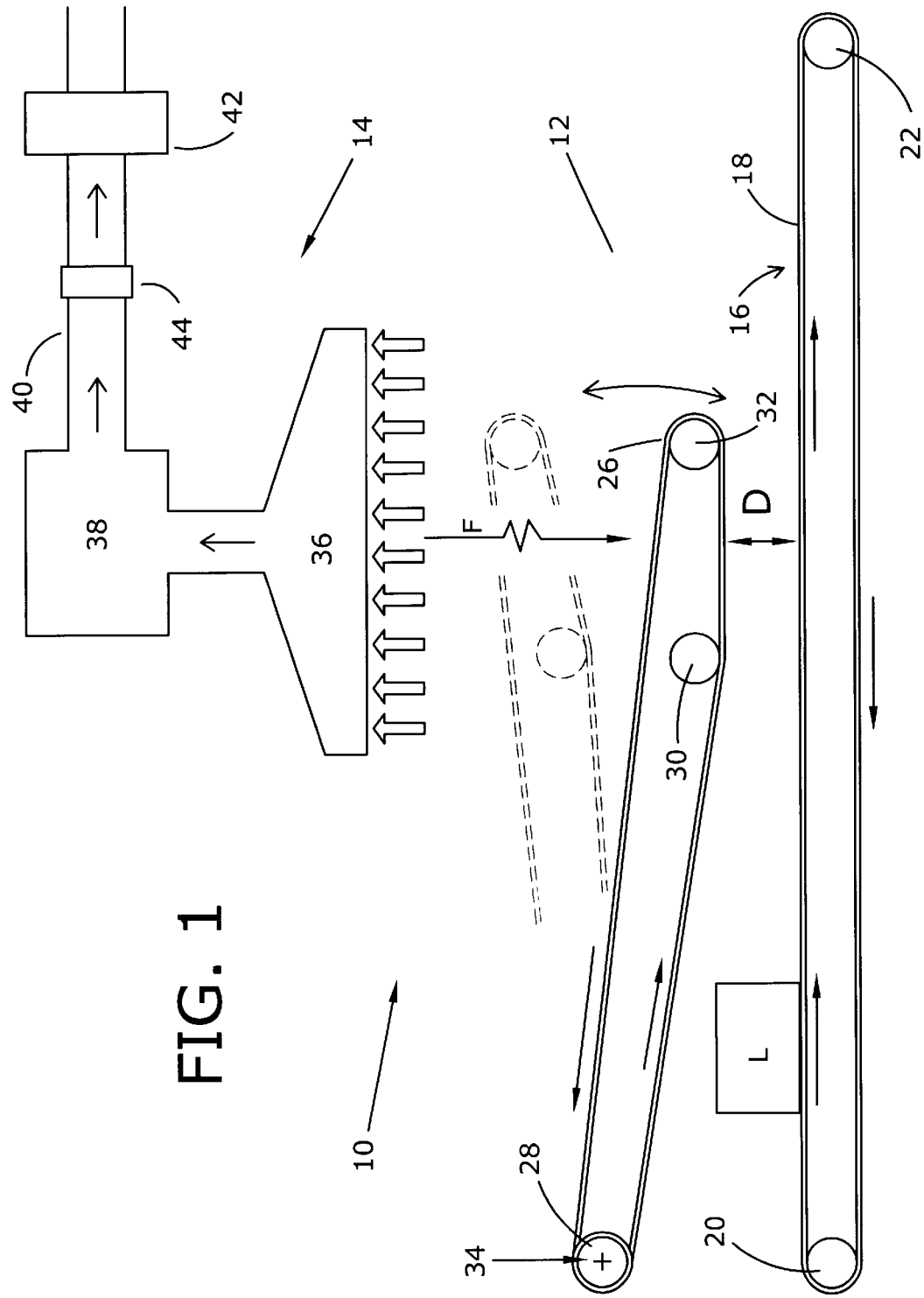
FIG. 1 is a side elevational view of a system for expelling test sample-volumes from luggage/packages in accordance with the present invention.

An exemplary system for expelling test sample-volumes from luggage/packages in accordance with the present invention is shown in a generalized form in FIG. 1 and designated generally therein by the reference character 10. In its preferred form, the system 10 is intended to process a continuous or near continuous stream of luggage or baggage-type articles and packages as typically used by airline, rail, and bus passengers. As is known, travelers use a wide variety of luggage, cases, carriers, bags, etc. to carry their possessions while traveling. Examples of these articles include hard-sided suitcases, soft-sided suitcases, suit carriers, shoulder bags, attaches, backpacks, and a variety of wheeled carriers. In general, the majority (if not the overwhelming majority) of luggage is fabricated from woven nylon or other synthetic material to form a 'soft-sided' article. In those types of luggage having internal frame structures, such as wheeled carts, it is not uncommon for the exterior of the luggage to be also fabricated from a heavy-duty fabric to provide a shape-sustaining article with resiliently yieldable panels.

The present invention contemplates that both fabric-based "softsided" luggage and molded plastic "hard-sided" luggage have, in general, sufficient shape-sustaining characteristic to define an interior volume for the articles carried in the luggage and to define various air spaces between those articles and any unoccupied spaces in the luggage. The shape of soft-sided luggage can be changed by merely applying a force thereto; it is thus possible to forcibly change and momentarily reduce the interior volume of the luggage to express a portion of the interior air therefrom. Since soft-sided luggage uses zippers and Velcro-type hook and loop closure systems, the luggage is air-permeable. In a similar manner, "hard-sided" luggage, while nominally presenting a hard plastic exterior, can be subject to an external force sufficient to momentarily depress or displace a side panel to reduce the interior volume thereof to express a portion of the interior air volume therefrom.

In those situations in which materials are being carried by the luggage have a particulate nature, such as anthrax spores, or materials that release atoms, molecules, or vapors into the enclosed air volume, the momentary compression of a luggage article that is susceptible to compression will cause a reduction in the interior volume and cause a portion of the interior air to be expelled from or otherwise expressed from the interior of the luggage through the various zippers, hook-and-loop fasteners, and the fabric from which the luggage is fabricated.

As can be appreciated, any air-entrainable particulates or atoms, molecules, or vapors within the interior of the luggage will be expelled into the surrounding ambient air.

In FIG. 1, the system 10 of the present invention is shown in one of several exemplary forms by a conveyor system 12 and a cooperating biohazard detection system 14.

The conveyor system 12 includes a first conveyor 16 having a belt 18 entrained between two spaced apart rollers 20 and 22 as is conventional. A drive motor (not shown) drives the belt 18 in the direction shown so that any luggage L mounted on the conveyor 16 will be moved from the left to the right.

A second conveyor 24 is positioned above the first conveyor 16 and is defined by a belt 26 entrained between various roller 28, 30, and 32. As in the case of the first conveyor 16, the second conveyor 24 includes a drive motor (not shown) that drives the belt 26 in the direction indicated. As indicated by the dotted-line illustration, the second conveyor 24 is pivotally mounted, for example, at 34, for pivotal motion toward and away from the underlying conveyor 16. The rightward end of the second conveyor 24 is resiliently biased downward toward the moving belt 18 of the first conveyor 16 by an adjustable spring system or by a combination of springs system and one or more weights, and, in its lowermost position, is spaced a selected distance "D" above the underlying conveyor 16. The arrangement of the conveyors is such that the spacing dimension "D" will vary (i.e., increase or decrease) as a function of the size of any luggage article L or package moved between the conveyors while the force F is applied to the luggage article L or package. Thus, the superposed conveyor is designed to "ride" the luggage articles L or packages and accommodate to their individual sizes while concurrently applying a compressive force F.

The detection system 14 includes an air intake hood 20 positioned above the conveyors and is designed to aspirate ambient air in the general vicinity of the conveyors and, more particularly, aspirate air immediately above those parts conveyors that will subject each piece of luggage or package to a compression force as that piece of luggage or articles passes between the moving belts of the two conveyors.

The air intake hood 36 of FIG. 1 connects directly to a sensing suite 38 which, in turn, connects through an outlet duct 40 to a filter, absorber, or scrubber 42 that removes any biohazard material prior to exhausting the air. An air mover 44, for example, an axial or radial flow fan, is located in the outlet duct 40 and has sufficient air moving capability to draw the air in the inlet of the air intake hood 36 into the biohazard sensing suite 38. The sensor suite 38 (typically including a plurality of diverse sensors) is connected to the air inlet hood 36 and is designed to accept the air drawn into the air intake hood 36 for analysis. The sensors can take the form, for example, of an ion mobility spectrometer-base sensor like the Barringer Technologies Ionscan 400B, for explosives, chemical warfare agents, and illicit drugs, the Joint Biological Point Detection System (JBPDS) manufactured by Intellitec of Jacksonville, Fla., and designed to detect a plurality of biological pathogens. It is contemplated that the sensor suite 38 will be suitable to detect air-entrainable particles, including bacteria, bacterial spores, viruses, rickettsia, toxins, low-volatility chemical particles including chemical warfare agent particles like VX, explosives particles, particles of illicit drugs, radioactive particles, and others, as well as vapors including chemical warfare agents, explosives and explosives-related compounds, illicit drugs, hazardous industrial chemicals, and others.

In normal operation, one or more articles of luggage L or packages are placed on the moving belt 18 of the conveyor 16 for transport from the left to the right toward the moving belt 26 of the pivotally mounted second conveyor 24. As the luggage L or package moves into the space or 'nip' defined between the two belts 18 and 26, the pivotally mounted conveyor 24 applies a resilient downward force F to the surfaces of the luggage or package. For those pieces of luggage or packages that have a measure of compressibility, viz., soft-sided or fabric pieces, the force applied by conveyor 24 will cause some reduction in the internal volume of the luggage or package; air from the interior volume will be expelled or otherwise expressed through zippered seams, pocket flaps, snap closures, and/or hook and loop closures from the interior the luggage or package into the immediately surrounding ambient air. Any particulates or vapors expressed into the ambient air will be drawn into the intake hood 36 for passage to and through the sensor suite 38. In a similar manner pieces of luggage that are nominally "hard-sided" will likewise undergo a compressive force sufficient to cause at least one panel to momentarily move or displace inwardly to momentarily reduce the interior volume thereof to express interior air therefrom.

In general, the minimum spacing "D" between the superposed conveyors 16 and 24 is selected to have the highest probability of engaging all anticipated luggage articles or packages to be subject to the compression step. Additionally, the downward resilient biasing force F is selected to effect a sufficient compression for all resiliently compressible articles as well as cause a momentary compression of at least one panel of "hard-sided" luggage.

FIG. 2 illustrates a variation of the superposed conveyors of FIG. 1; in FIG. 2, opposed pivotally mounted conveyors 24' and 24" are positioned on opposite lateral sides of the conveyor 16 and mutually resiliently biased toward one another to 'capture' and apply a squeezing compressive force to any luggage articles or packages moving of the conveyor 16 and thereby express or expel a portion of the interior air volume from the luggage article or package.

While FIG. 2 shows the use of two pivotally mounted and resiliently biased conveyors, one of those two conveyors can be replaced, for example, by a stationary guide plate 46, as represented in FIG. 3.

The embodiments of FIGS. 1–3 use moving belts to both convey and to effect a momentary compression of the luggage articles or packages. As can be appreciated, a controlled compression can be achieved in other ways. For example and as shown in FIG. 4, a 'presser' plate 50 is mounted for reciprocal motion toward and away from a guide plate 52. A fluidic cylinder 54 (e.g., pneumatic) is connected to the presser plate 50 and controlled to effect reciprocal motion to press each piece of luggage or package moving from the left to the right on the conveyor 18.

As shown in FIG. 5, the presser plate 50 of FIG. 5 can be replaced by a bellows assembly 60 that is fluidically operated to expand toward and away from a guide plate 62 to effect controlled and resilient compression of each luggage article or package that is transported along the conveyor. As represented in dotted-line illustration in FIG. 5, the guide plate 62 can be replaced by a second bellows assembly 60' and both operated in unison to effect the desired compression step. In general, the bellows assembly is fabricated from a resilient rubber-like elastomer with conventional corrugations 64 and a surface 66 intended to engage and resiliently press against each luggage article or package moving on the conveyor 18.

Figure 7:
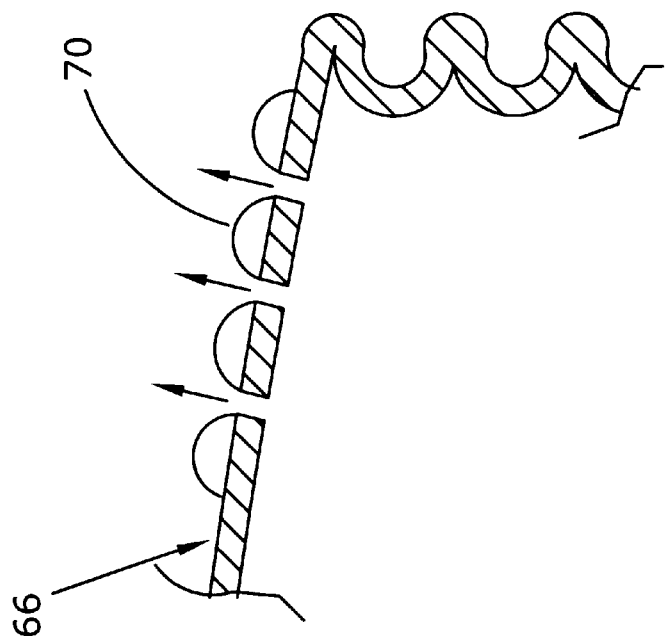
FIG. 7 is an enlarged detail of a portion of the fluidically expansible bellows of FIG. 5 showing optional air-bleed holes and bumper-like protrusions or extensions.
Figure 6:
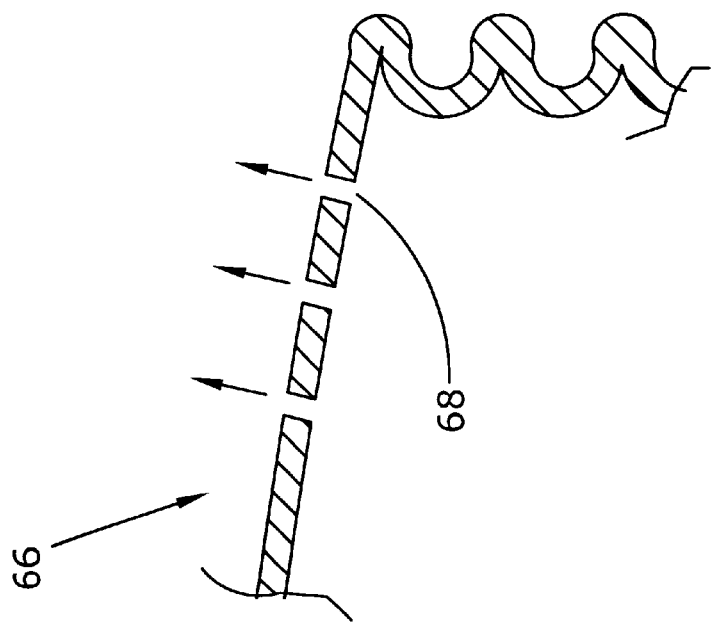
FIG. 6 is an enlarged detail of a portion of the fluidically expansible bellows of FIG. 5 showing optional air-bleed holes.

As shown in both FIGS. 6 and 7, that portion of the bellows assembly 60 that faces the to-be-compressed luggage articles or packages can include a plurality of 'bleed' holes 68 so a portion of the air used to inflate the bellows assembly 60 also introduces air flow turbulence in the general vicinity of the luggage articles or packages to assist in further energizing or aerosolizing any particulates ejected consequent to the compression step. As shown in FIG. 7, protrusions or bumpers 70 can be formed on that part of the bellow assembly 66 intended to engage the luggage pieces or packages to assist in 'poking' the luggage pieces to reduce their interior volume sufficient to express or expel some of the interior air volume for testing.

Each of the embodiments described above function to provide a compression force to the luggage article or piece.

In FIGS. 8 and 8A, the system is designed to provide multiple compression forces as well as more closely conform the application of the compression force to the 'topology' of the luggage article or piece L. More specifically and as shown in FIG. 8, the system 100 includes a first and at least one other station, S1 and S2, that are arranged in sequence above the lower moving belt 102. An upper moving belt 104 is superposed above the lower moving belt 102 and is entrained about the stations S1, S2, . . . , Sn−1, Sn as described below.

Each station includes one or more compression modules CM that are designed to engage the surfaces of the luggage articles or packages L; in the case of FIG. 8, each station includes three compression modules CM. As shown in FIG. 8A, each compression module CM is defined by a housing H that engages a plenum P through a slip-joint (unnumbered) for limited upward and downward motion. The lower end of each housing is open to and spanned by the moving belt 104. A plurality of cylindrical bodies of revolution 106 (i.e., cylinders, rollers, or the like) are confined by the moving belt 104; however, the weight of each cylinder 106 and the tension on the moving belt 104 are controlled to allow the individual cylinders 106 to move upward and downward as a function of the particular shape of any luggage piece or article moving beneath the moving belt 104.

As shown in FIG. 8, a luggage article or package L moves along the belt 102 with the upper edge of the luggage article or package L contacting the upper moving belt 104; the luggage piece or article L is then 'captured' between the two belts, 102 and 104, and transported beneath the first station S1 where each compression module CM moves upward (or downward) to accommodate the overall size the luggage article or package. Additionally, the cylinders 106 also move upward or downward to conform to the shape of the luggage article or package L and effectively "roll-over" or "knead" the luggage article L to apply the desired compressive or volume-reducing force.

Once the luggage article or package is processed by the first station S1, the luggage article has an opportunity to restore is original shape and ingest ambient air as shown in dotted line illustration in the inter-station area of FIG. 8. Thereafter, the luggage article is then subject to further compressive or volume reducing forces in the second station S2. As can be appreciated, the number of stations can be increased as desired.

The plenums P can be pressurized, if desired, to provide a controllable downward compression force on the luggage articles L, or, in the alternative, can function as the air intake hood or cowling to direct the test-volume sample to the sensor suite of FIG. 1.

The system of FIG. 8 allows the luggage article or package to effectively breath (i.e., inhale and exhale) as part of the processing to increase the probability that an adequate test sample-volume will be obtained. Additionally, the system of FIG. 8 also accommodates to variations in the external form-factor of the luggage article or package undergoing inspection.

Another embodiment of the present invention is shown in FIG. 9 and is designed to embrace each luggage article or package L in a constrictable pressurized elastic 'cuff' or bladder B. The bladder B can be fabricated from a non-permeable, semi-permeable, or controlled permeability fabric in a manner analogous to a medical pressure cuff and is designed, upon inflation, to embrace all or a substantial portion of the exterior sides of the luggage article or package L and provide both a compressive or volume-reducing force that conforms to or substantially conforms to the exterior topology and irregularities of the luggage article under inspection.

The test sample-volumes extracted from the luggage article L are vented to the conduit 40 with a portion thereof directed to the sensor suite 38 for analysis and thereafter directed to the exhaust filter 42. A fan 44 provides the motive power for moving the air flows.

As shown in FIG. 9A, the fabric or material from which the bladder B is fabricated can be formed with a 'bumped' surface with interstitial air-bleed holes in the same or a similar manner as described above in relationship to FIG. 7.

Figure 11:
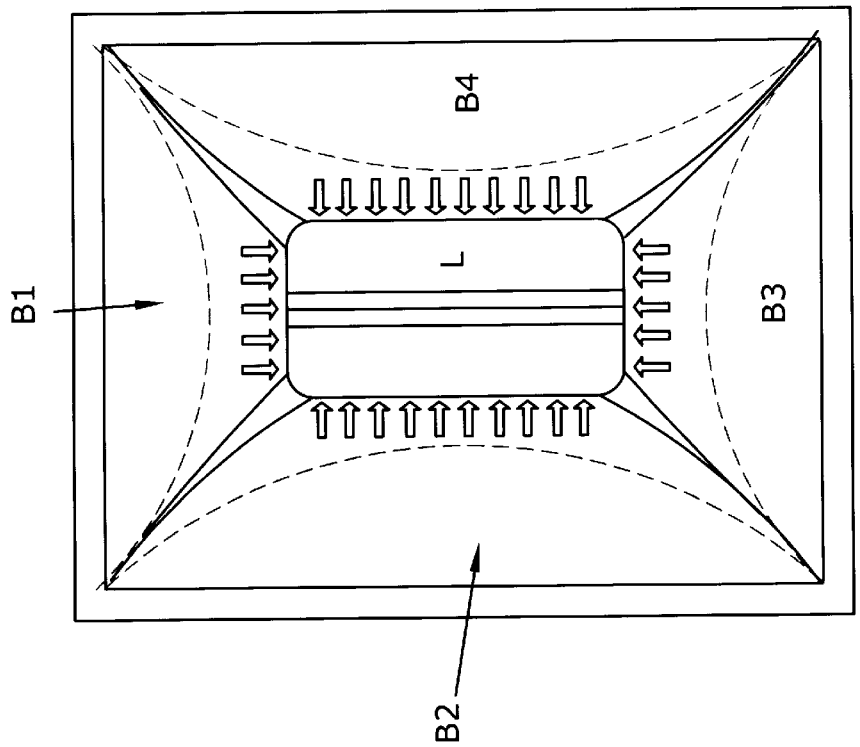
FIG. 11 illustrates the expansible multi-bladder or chamber system of FIG. 10 in its fully expanded or deployed.
Figure 10:
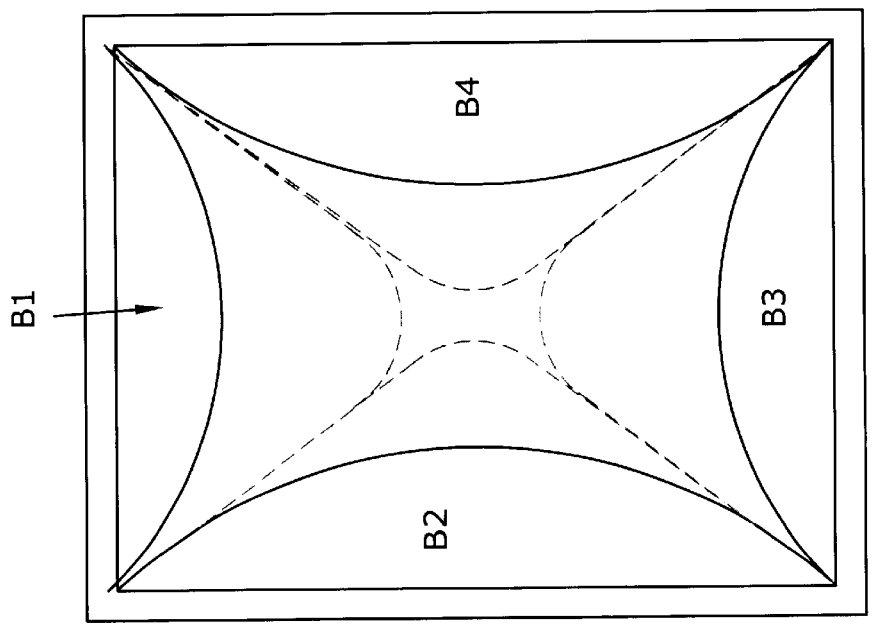
FIG. 10 is another example of an expansible multi-bladder or chamber system by which multiple sides of a luggage article or package are subjected to a compression force.

FIGS. 10 and 11 represent yet another version of the present invention in which a frame is provided with four inwardly facing expansion bladders B1, B2, B3, B4 arrayed to engage and conform to the surface irregularities of the respective sides of any luggage article or package under inspection. As presented by the solid and dotted-line illustrations in FIG. 10, each of the bladders is inflatable between an uninflated or 'relaxed' state (solid-line illustration) and a fully extended or inflated state (dotted-line illustration). As shown in FIG. 11, when the individual bladders are inflated, a respective surface portion of the luggage article or package L is engaged by a compressive force that serves to effect a controlled compression or reduction in the interior volume of the luggage article or package L.

As can be appreciated, the embodiments of FIGS. 9–11 allow a luggage article or package under inspection to be subject to multiple compression/relaxation sequences.

Figure 12:
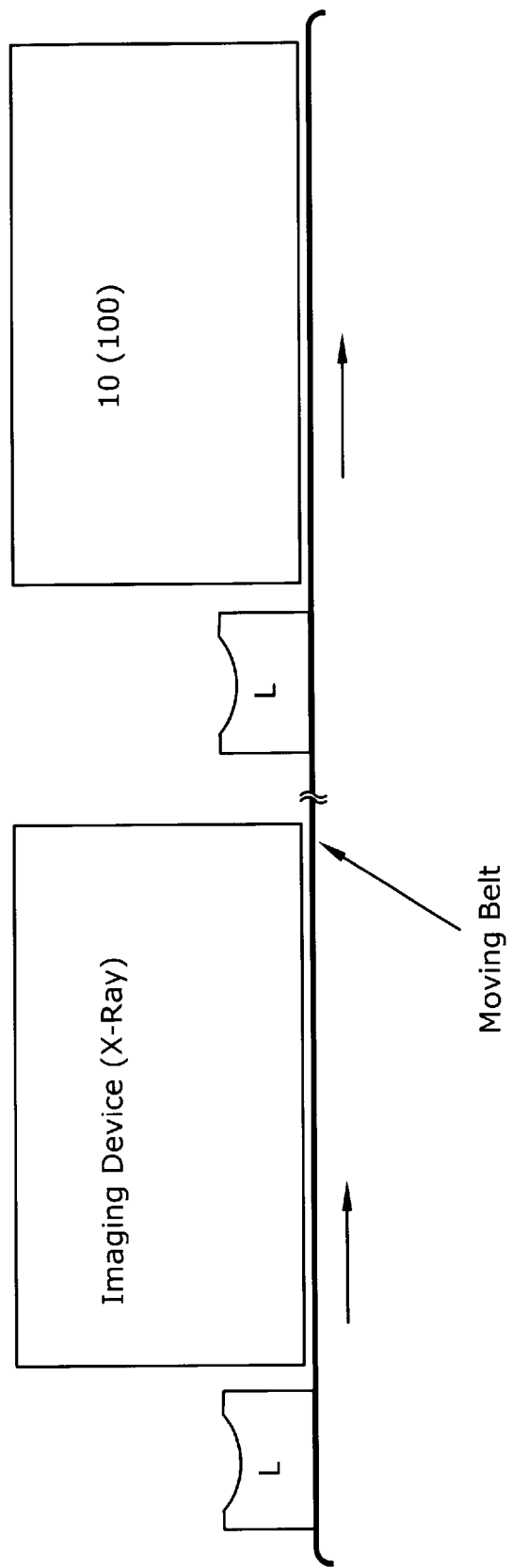
FIG. 12 is an illustrative diagram showing an embodiment of the present invention in combination with a imaging machine, such as an X-ray machine.

One or more of the above described embodiments can be implemented in stand-alone applications or in parallel or in conjunction with other devices like conventional X-Ray imaging systems for detecting weapons, batteries, wiring or explosive detonators, etc. For example and as shown in FIG. 12, a conventional X-ray imager 200 is shown in a position in advance of the embodiment(s) of the present invention. In operation, each luggage article or package would be imaged in the imaging machine and then advanced into the system of the present invention. As can be appreciated, those embodiments of the present invention that transport the luggage articles or packages on a moving belt optimally cooperate with imaging machines in current use.

The present invention advantageously provides a method and system for expelling test sample-volumes from luggage/packages to allowing testing for biohazard materials. The present invention is particularly suited for those situations in which a large continuous stream of luggage articles or packages must be inspected.

As will be apparent to those skilled in the art, various changes and modifications may be made to the illustrated method and system for expelling test sample-volumes from luggage/packages of the present invention without departing from the spirit and scope of the invention as determined in the appended claims and their legal equivalent.

What is claimed is:

1. A system for testing luggage articles and/or packages for undesired or proscribed materials, comprising:

means for momentarily reducing the internal volume of a luggage article or package sufficient to express a portion of the internal air volume therefrom, said means including a guide plate and a resilient bladder that expands and contracts in response to fluid pressure, the bladder having a resiliently displaceable surface portion thereof to resiliently engage any luggage article or package positioned between said resiliently displaceable surface and said guide plate to express a portion of the internal air volume therefrom upon expansion of the resilient bladder; and means for subjecting the expressed air to an analysis for any undesired or proscribed materials.

2. The system of claim 1, wherein said surface portion has a permeability characteristic to pass a portion of a pressurized fluid in the resilient bladder therethrough.

3. The system of claim 2, wherein said surface portion has a plurality of holes therethrough to pass a portion of a pressurized fluid in the resilient bladder therethrough.

4. The system of claim 1, wherein said surface portion has surface irregularities to engage a surface of a luggage article or package.

5. The system of claim 1, wherein said surface portion has a plurality of projecting bumps thereon to engage a surface of a luggage article or package.

6. The system of claim 1, wherein said surface portion has a plurality of projecting bumps thereon to engage a surface of a luggage article or package and a plurality of holes therethrough to pass a portion of a pressurized fluid in the resilient bladder therethrough.

7. A system for testing luggage articles and/or packages for undesired or proscribed materials, comprising:

means for momentarily reducing the internal volume of a luggage article or package sufficient to express a portion of the internal air volume therefrom, said means including a pressurizable bladder having surface portions thereof for engaging opposite sides of a luggage article or package upon pressurization to express a portion of the internal air volume therefrom and means for subjecting the expressed air to an analysis for any undesired or proscribed materials.

8. The system of claim 7, wherein said surface portion has a permeability characteristic to pass a portion of a pressurized fluid in the resilient bladder therethrough.

9. The system of claim 7, wherein said surface portion has a plurality of holes therethrough to pass a portion of a pressurized fluid in the resilient bladder therethrough.

10. The system of claim 7, wherein said surface portion has surface irregularities to engage a surface of a luggage article or package.

11. The system of claim 7, wherein said surface portion has a plurality of projecting bumps thereon to engage a surface of a luggage article or package.

* * * * *